(12) United States Patent
Hamel et al.

(10) Patent No.: US 12,274,864 B2
(45) Date of Patent: Apr. 15, 2025

(54) INJECTOR

(71) Applicant: Duoject Medical Systems Inc., Bromont (CA)

(72) Inventors: Simon Hamel, Knowlton (CA); Marie Lafontaine Lacasse, Sherbrooke (CA)

(73) Assignee: DUOJECT MEDICAL SYSTEMS, INC., Quebec (CA)

( * ) Notice: Subject to any disclaimer, the term of this patent is extended or adjusted under 35 U.S.C. 154(b) by 719 days.

(21) Appl. No.: 17/300,571

(22) PCT Filed: Feb. 20, 2020

(86) PCT No.: PCT/CA2020/000018
§ 371 (c)(1),
(2) Date: Aug. 20, 2021

(87) PCT Pub. No.: WO2020/168412
PCT Pub. Date: Aug. 27, 2020

(65) Prior Publication Data
US 2022/0323683 A1    Oct. 13, 2022

(30) Foreign Application Priority Data
Feb. 22, 2019   (CA) .................... CA 3034664

(51) Int. Cl.
*A61M 5/32* (2006.01)
*A61M 5/315* (2006.01)
*A61M 5/50* (2006.01)

(52) U.S. Cl.
CPC ...... *A61M 5/31501* (2013.01); *A61M 5/3202* (2013.01); *A61M 2005/3265* (2013.01)

(58) Field of Classification Search
CPC ............ A61M 5/31501; A61M 5/3202; A61M 5/3257; A61M 5/50; A61M 2005/3265
See application file for complete search history.

(56) References Cited

U.S. PATENT DOCUMENTS

| | | | |
|---|---|---|---|
| 2005/0065482 A1* | 3/2005 | Hauri | A61M 5/3202 604/263 |
| 2009/0209903 A1* | 8/2009 | Cherif-Cheikh | A61M 37/0069 604/63 |
| 2017/0165423 A1* | 6/2017 | Holland | A61M 5/31511 |
| 2019/0009026 A1* | 1/2019 | Gonzalez | A61M 5/326 |
| 2021/0146058 A1* | 5/2021 | Shetty | A61M 5/31551 |

\* cited by examiner

*Primary Examiner* — Courtney B Fredrickson
*Assistant Examiner* — Haden Matthew Ritchie
(74) *Attorney, Agent, or Firm* — MEDLER FERRO WOODHOUSE & MILLS PLLC

(57) ABSTRACT

An injector comprising an outer housing, a generally longitudinally extending keyway formed in the outer housing, an inner housing located interiorly of the outer housing, a guide member mounted at one end of the inner housing, the guide member having at least one protrusion adapted to engage the keyway, a spring member, the spring member having a first end abutting the outer housing, a second end of the spring member abutting the guide member, a syringe mounted interiorly of the inner housing, a needle mounted on one end of the syringe, the syringe having a plunger and a plunger rod, a finger rest member mounted over the outer housing, the finger rest member being opaque to thereby prevent visual access to the keyway.

6 Claims, 7 Drawing Sheets

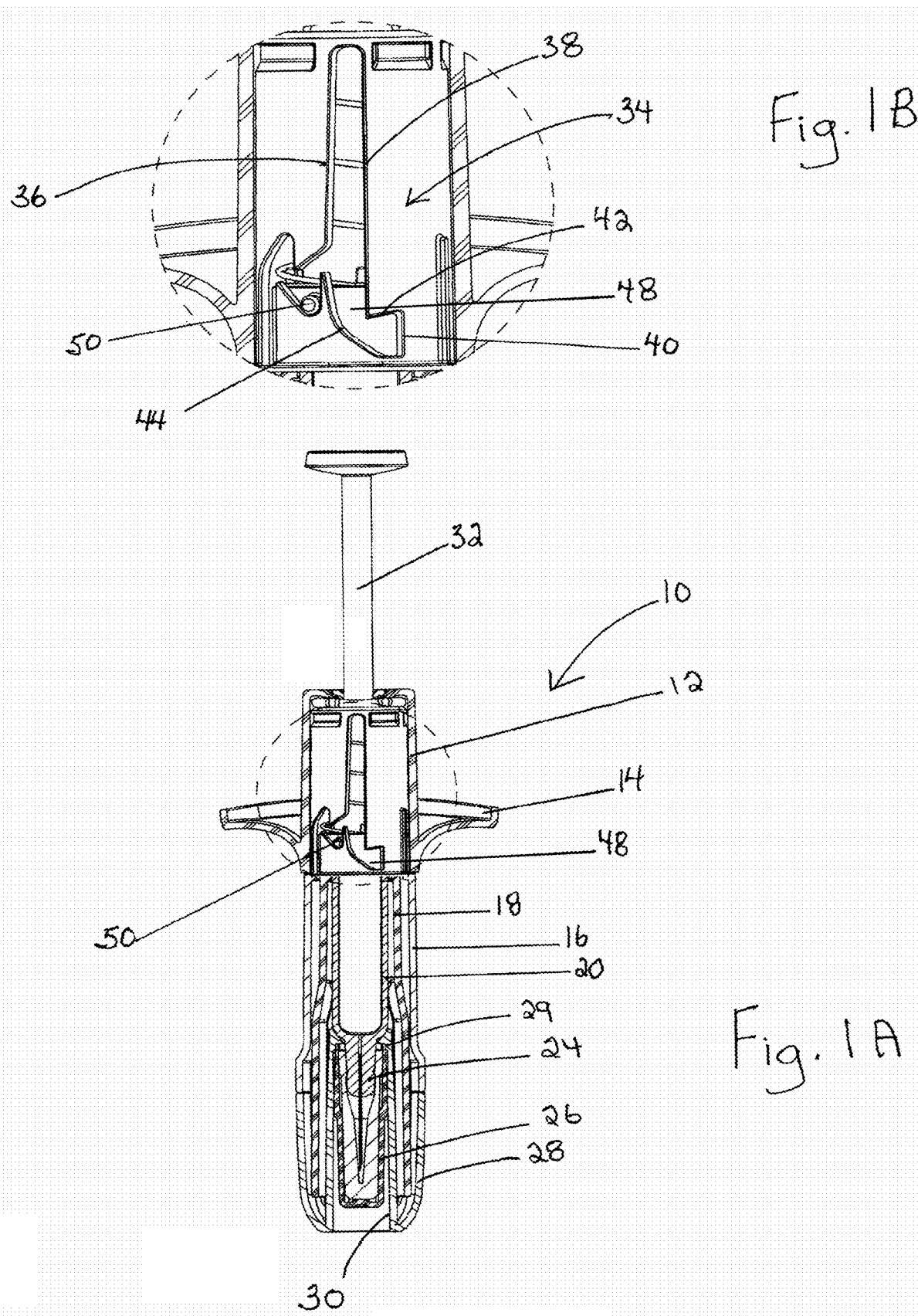

INJECTOR

FIELD OF THE INVENTION

The present invention relates to an injection device and more particularly, relates to an injection device having multiple features to provide safety to the user.

BACKGROUND OF THE INVENTION

The problem of syringe needle stick is well known in the art. A needle stick occurs when the needle penetrates the skin unintentionally. This occurs for injection, a drug may be accidentally injected into a person other than the intended recipient. Needle stick occurs after use of a syringe for an injection. This is equally dangerous as it is possible to contract a disease from a used needle. This can result in an infection such as hepatitis or HIV.

The present invention provides an injector which provides a number of safety features to prevent accidental needle stick.

It is an object of the present invention to provide an injector which has multiple safety features to prevent accidental needle stick and also to prevent wrongful use of the injector.

SUMMARY OF THE INVENTION

According to one aspect of the present invention, there is provided an injector comprising an outer housing, a generally longitudinally extending keyway formed in said outer housing, an inner housing located interiorly of said outer housing, a guide member mounted at one end of said inner housing, said guide member having at least one protrusion adapted to engage said keyway, a spring member, said spring member having a first end abutting said outer housing, a second end of said spring member abutting said guide member, a syringe mounted interiorly of said inner housing, a needle mounted on one end of said syringe, said syringe having a plunger and a plunger rod, a finger rest member mounted over said outer housing, said finger rest member being opaque to thereby prevent visual access to said keyway.

The injector of the present invention is designed to prevent tampering. Tampering is always a problem in that an interested party will attempt to see how the mechanism works and how the safety features can be by-passed. Accordingly, the present invention provides an opaque cover over the operating mechanism to prevent such tampering.

A further problem with some syringes is that the piston rod can be detached. The injector of the present invention prevents this happening.

The injector of the present invention also provides a visible signal that the syringes have not been used or tampered with.

The injector of the present invention is designed to prevent cross-contamination.

The injector of the present invention may be used for many different types of injections, including intramuscular, sub-cutaneous, intravenous and intradermal injections. Although most injections are administered by trained medical personnel, in some instances, and particularly those formulated for intramuscular injection, the patients themselves may do the injection.

BRIEF DESCRIPTION OF THE DRAWINGS

Having thus generally described the invention, reference will be made to the accompanying drawings illustrating embodiments thereof, in which:

FIG. 1A is a sectional view showing the injector before removal of the cap;

FIG. 1B is an enlarged view of the portion in a circle of dashed lines of FIG. 1A;

DETAILED DESCRIPTION OF THE INVENTION

Figure 2B:
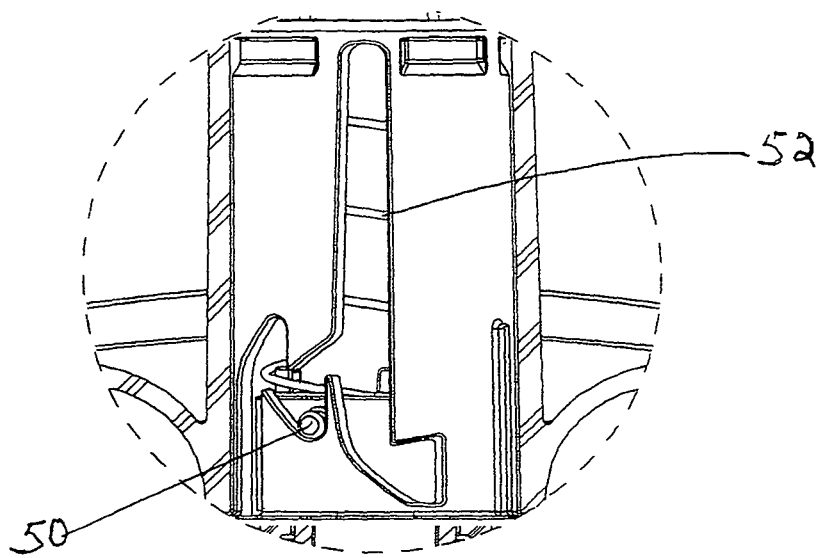
FIG. 2B is an enlarged view of the portion in a circle of dashed lines of FIG. 2A.

Referring to the drawings in greater detail and by reference characters thereto, there is illustrated an injection generally designated by reference numeral 10. Injection device 10 may be utilized for injection a fluid into a target, the target frequently being a patient and the injector delivering a drug or medication.

Injector 10 includes a finger rest member 12 having flanges 14 being located at the upper end thereof. Preferably, finger rest member 12 is opaque to present visual access to the inner portions of the device.

Injector 10 has an outer housing 16 and an inner housing 18. Both inner housing 18 and outer housing 16 are non circular and therefor cannot rotate completely within one another. Mounted interiorly of inner housing 18 is a pro-filled syringe 20 containing the substance (drug) to be injected from the injector. Pre-filled syringe 20 includes a needle 22 affixed within a needle hub 24. There is a needle shield 26 which surrounds needle 22.

A cap is comprised of a cap outer wall 28 and a cap inner wall 30 which engages on the end of the injector with cap outer wall 28 lying adjacent inner housing 18 and cap inner wall 30 extending upwardly and has small flanges 29 to engage with the end of needle shield 26.

A keyway generally designated by reference numeral 34 is provided in the wall of outer housing 16. Keyway 34 is defined by a first side wall 36, and a second side wall 38 and lower side wall 40. Keyway 34 also includes a lower somewhat horizontal wall 42 and a lower side wall 44.

A guide member 48 is secured to inner housing 18, guide member 48 is provided with protrusions 50 which are designed to engage within keyway 34 as will be described in greater detail hereinbelow. It will be understood that a similar arrangement can be provided on the opposite side.

Figure 2A:
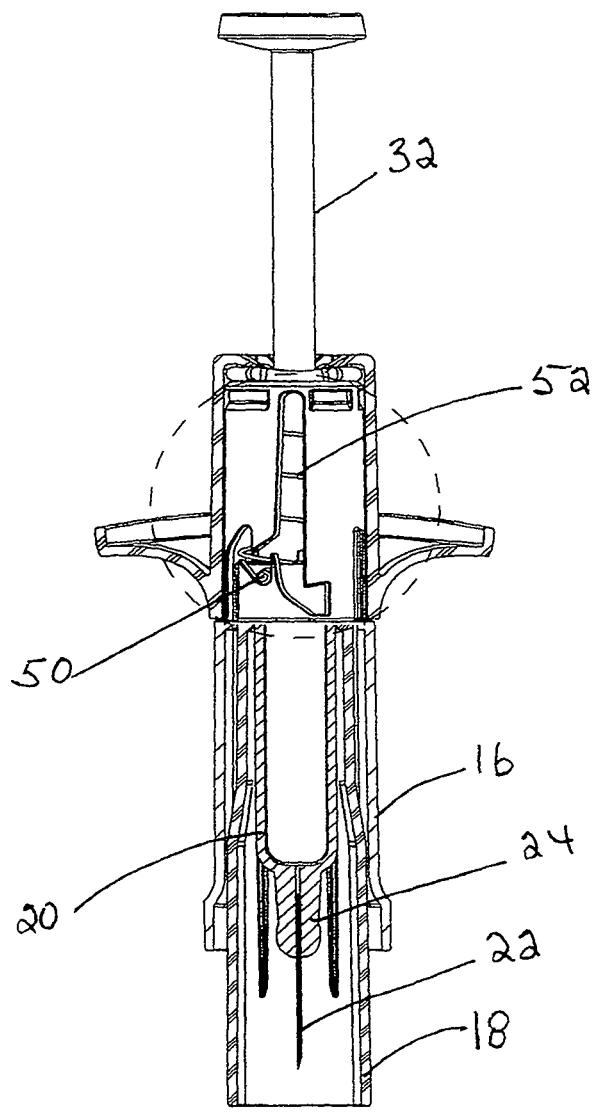
FIG. 2A is a sectional view showing the injector device after removal of the cap.

A spring 52 is mounted within outer housing 16 and abuts one end of outer housing 16 and the other end of the spring abutting guide member 48. In the first step, as shown in FIGS. 1A and 1B, the cap is in place to allow secure transport of the device. When preparing the injector for use, cap 28 is removed by pulling the cap straight to remove it to leave the position shown in FIGS. 2A and 2B. In this position, the fluid path is open and needle 22 is accessible while needle shield 26 is removed by small flanges 29.

Figure 3B:
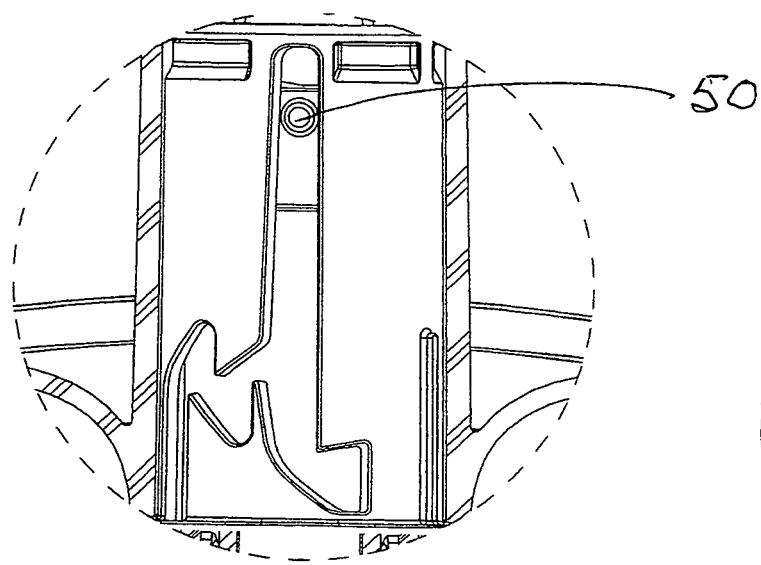
FIG. 3B is an enlarged view of the portion in a circle of dashed lines of FIG. 3A.
Figure 3A:
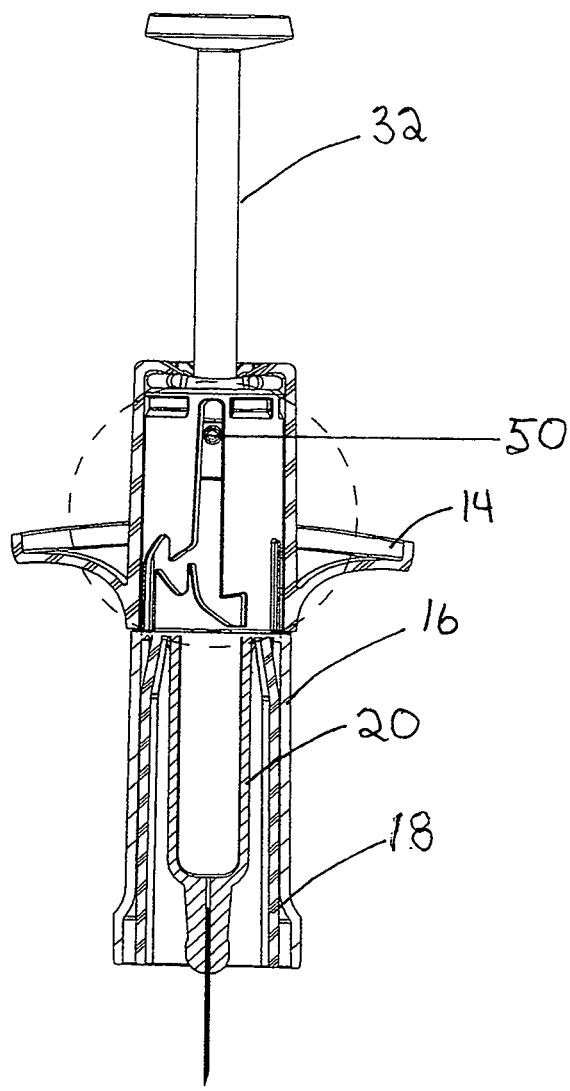
FIG. 3A is a sectional view illustrating insertion of the needle into a patient.
Figure 4B:
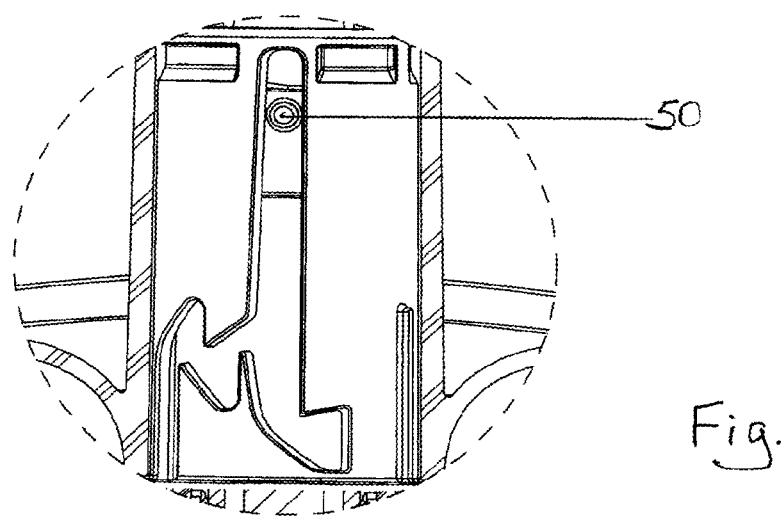
FIG. 4B is an enlarged view of the portion in a circle of dashed lines of FIG. 4A.
Figure 4A:
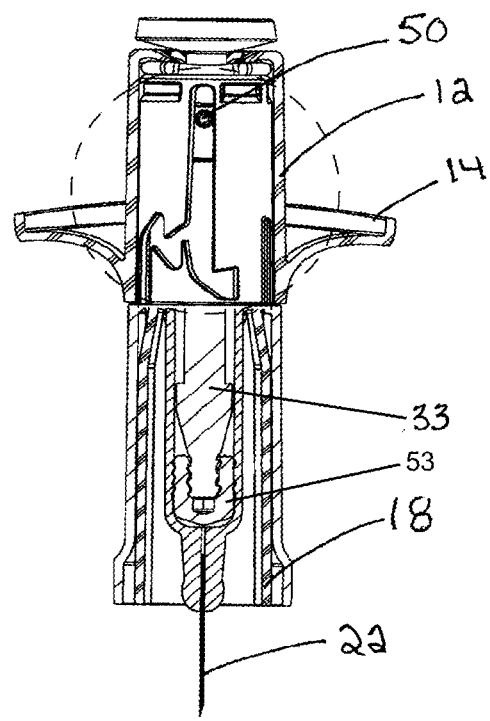
FIG. 4A is a cross-sectional view illustrating the injector as it finishes injecting the fluid into the patient.
Figure 5B:
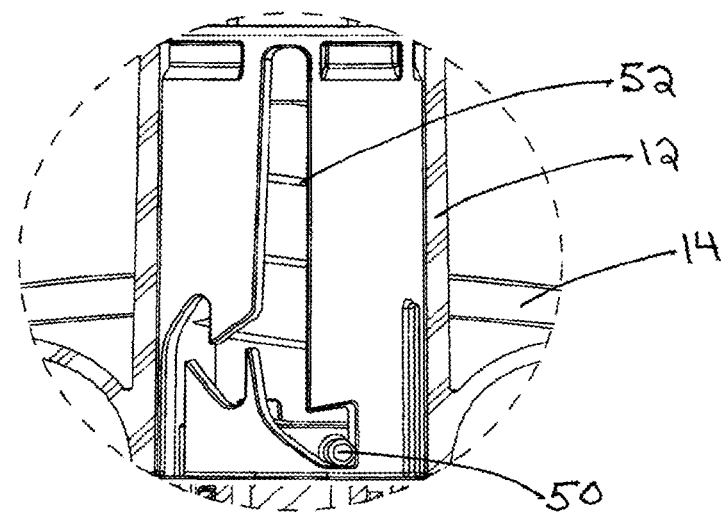
FIG. 5B is an enlarged view of the portion in a circle of dashed lines of FIG. 5A.
Figure 5A:
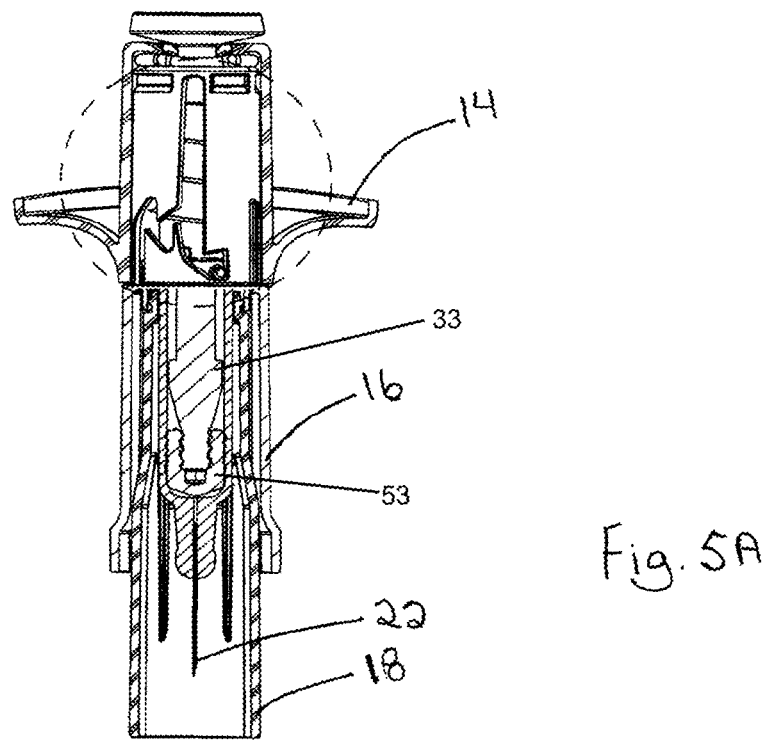
FIG. 5A is a sectional view of the injector following the extraction of the needle from the patient.
Figure 6B:
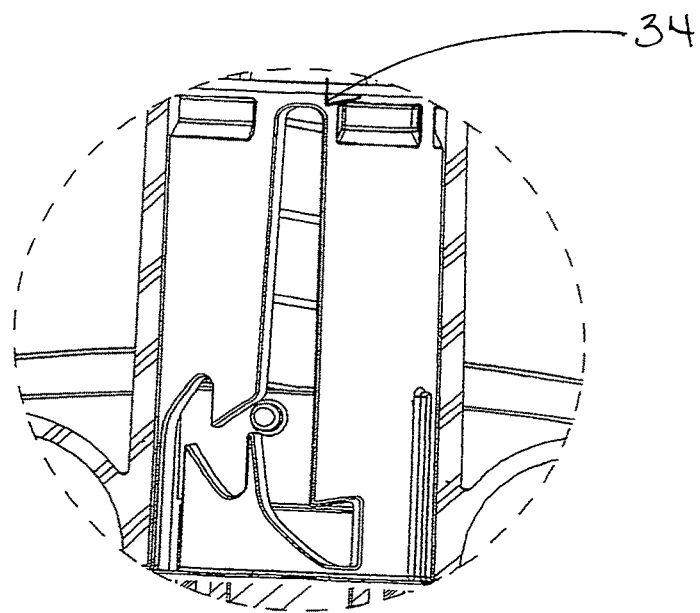
FIG. 6B is an enlarged view of the portion in a circle of dashed lines of FIG. 6A.
Figure 6A:
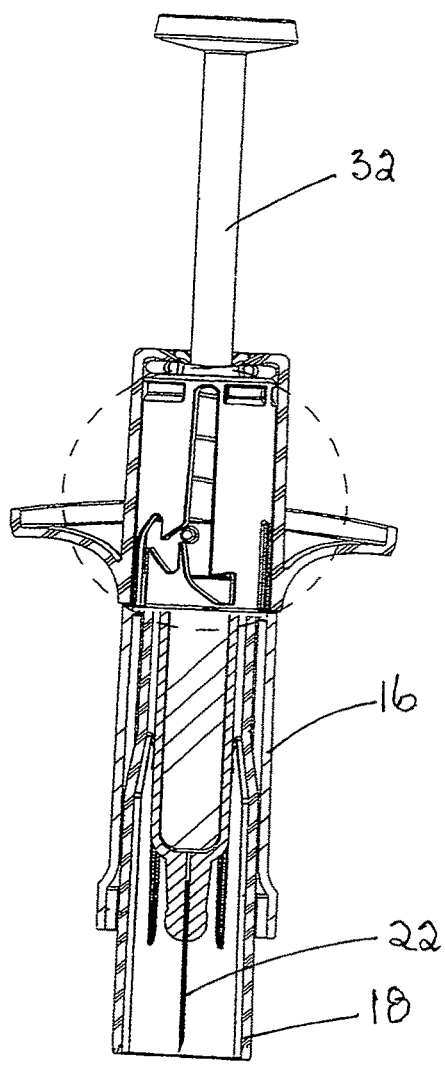
FIG. 6A is a side view illustrating the injector's safety activation mechanism.
Figure 7:
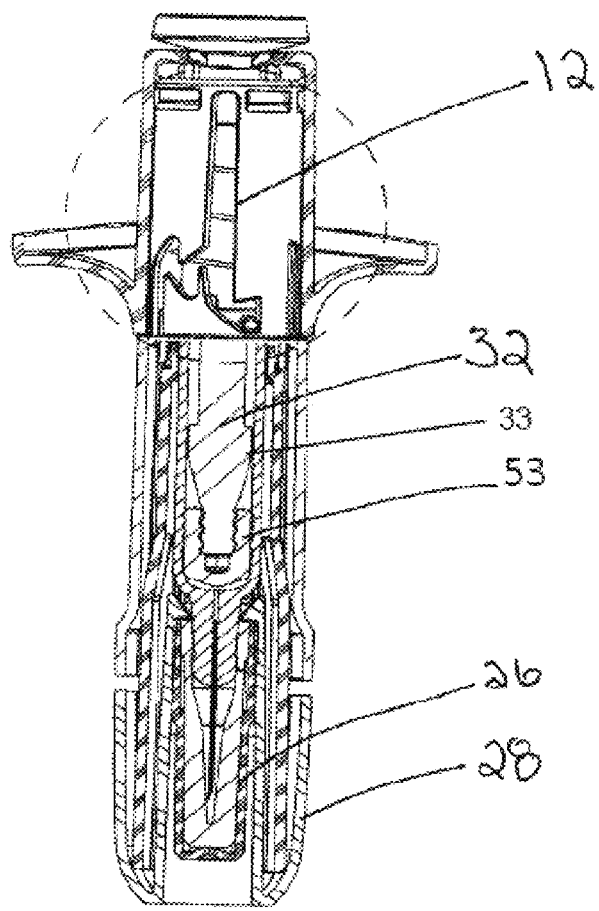
FIG. 7 is a side elevational view illustrating the injector following injection and placement of the cap thereon.

As shown in FIGS. 3A and 3B, when the inner housing 18 is pushed against a resilient surface, it retracts into the housing in an axial displacement. Guide member 48 has protrusions 50 which will be guided by keyway 34 such that protrusion 50 is at the top of keyway 34. Guide member 48 can rotate in keyway 34 due to a swivel snap attachment to inner housing 18. During the pressing of inner housing 18, spring 52 is compressed.

In order to inject the contents of syringe 20, plunger rod 32 is depressed and plunger 53 causes the contents of pre-filled syringe 20 to be expelled or injected. Plunger rod 32 is screwthreadably engaged with plunger 53 and includes an enlarged portion 33 to prevent removal from finger rest member 12. Following the injection, spring 52 will extend and protrusions 50 will fall to a lower portion of the keyway into a locked position. Simultaneously, the inner housing 18 will extend axially out of the housing to permanently cover needle 22 since protrusion 50 is unable to move upwardly due to wall 42.

Thus, the keyway 34 can be formed either as a cutout in the wall of the outer housing 16 or as a groove formed in the wall thereof. Also, it should be noted that plunger rod 32 cannot be withdrawn through finger rest member 12.

It will be understood that the above described embodiment is for purposes of illustration only and that changes and modifications may be made thereto without departing from the spirit and scope of the invention.

The embodiments of an invention in which an exclusive property or privilege is claimed is defined as follows:

1. An injector comprising:
   an outer housing, a generally longitudinally extending keyway formed in said outer housing, said keyway comprising an elongated top portion above an enlarged lower portion with an adjacent side portion;
   an inner housing located interiorly of said outer housing;
   a guide member mounted at one end of said inner housing, said guide member having at least one protrusion adapted to engage said keyway;
   a spring member, said spring member having a first end abutting said outer housing, a second end of said spring member abutting said guide member;
   a syringe mounted interiorly of said inner housing,
   a needle mounted on one end of said syringe;
   said syringe having a plunger and a plunger rod;
   a finger rest member mounted over said outer housing, said finger rest member being opaque to thereby prevent visual access to said keyway;
   wherein said at least one protrusion engages the adjacent side portion of said keyway prior to use of the injector;
   wherein said at least one protrusion engages the top portion of said keyway if the inner housing is pushed;
   wherein said at least one protrusion engages the enlarged lower portion of said keyway if the inner housing is pushed and then released;
   and wherein the enlarged lower portion further comprises a somewhat horizontal wall such that when said at least one protrusion engages the enlarged lower portion, said at least one protrusion is blocked from moving out of the enlarged lower portion.

2. The injector of claim 1 wherein said plunger rod extends through said finger rest member, said plunger rod having an enlarged portion to prevent removal thereof.

3. The injector of claim 1 wherein said finger rest member is visible when said injector has been activated.

4. The injector of claim 1 wherein said finger rest member includes first and second flanges extending outwardly therefrom.

5. The injector of claim 1 wherein said plunger rod is screw threadably engaged with said plunger.

6. The injector of claim 1 wherein said inner housing and said outer housing are each noncircular in configuration.

* * * * *